United States Patent [19]
Runeman et al.

[11] Patent Number: 5,391,160
[45] Date of Patent: Feb. 21, 1995

[54] DISPOSABLE ABSORBENT ARTICLE WHICH COMPRISES A HOSE-LIKE ABSORPTION BODY

[75] Inventors: Bo Runeman, Partille; Peter Rönnberg, Mölndal, both of Sweden

[73] Assignee: Mölnlycke AB, Göteborg, Sweden

[21] Appl. No.: 242,333

[22] Filed: May 13, 1994

Related U.S. Application Data

[63] Continuation of Ser. No. 1,923, Jan. 7, 1993, Pat. No. 5,342,337, which is a continuation of Ser. No. 773,969, Nov. 15, 1991, abandoned.

[30] Foreign Application Priority Data

May 16, 1989 [SE] Sweden .................. 8901739

[51] Int. Cl.⁶ .............................................. A61F 13/46
[52] U.S. Cl. .................... 604/378; 604/385.1
[58] Field of Search ............ 604/378, 379, 384, 385.1

[56] References Cited

U.S. PATENT DOCUMENTS

| | | | |
|---|---|---|---|
| 4,505,705 | 3/1985 | Matthews et al. | 604/385.1 |
| 4,795,453 | 1/1989 | Wolfe | 604/385.1 |
| 4,895,568 | 1/1990 | Enloe | 604/385.2 |
| 4,973,325 | 11/1990 | Sherrod et al. | 604/368 |
| 5,324,278 | 6/1994 | Visscher et al. | 604/378 X |

FOREIGN PATENT DOCUMENTS

| | | |
|---|---|---|
| 82540/82 | 2/1983 | Australia . |
| 0122803 | 10/1984 | European Pat. Off. . |
| 0173068 | 3/1986 | European Pat. Off. . |
| 0223486 | 5/1987 | European Pat. Off. . |
| 0343941 | 11/1989 | European Pat. Off. . |
| 2124907 | 2/1984 | United Kingdom . |

*Primary Examiner*—David Isabella
*Assistant Examiner*—Mary Beth O. Jones
*Attorney, Agent, or Firm*—Burns, Doane, Swecker & Mathis

[57] ABSTRACT

A disposable absorbent article, such as a diaper or an incontinence guard, includes an inner liquid-permeable casing sheet which is positioned nearest the body of the wearer when the article is worn, an outer liquid-permeable casing sheet, and an absorbent pad enclosed between the inner and outer casing sheets. The absorbent pad includes, at least in the crotch part of the article, a hose-like body that is comprised of a shape-stable material having a very high liquid permeability. The hose-like body is generally centrally positioned in the article and extends in the longitudinal direction of the article. The hose-like body borders on the inner casing sheet and is surrounded by absorbent material on at least the side thereof remote from the inner casing sheet. The article can also include liquid barriers positioned on respective sides of the hose-like body.

13 Claims, 2 Drawing Sheets

DISPOSABLE ABSORBENT ARTICLE WHICH COMPRISES A HOSE-LIKE ABSORPTION BODY

This application is a continuation of application Ser. No. 08/001,923, filed Jan. 7, 1993, now U.S. Pat. No. 5,342,337, which is a continuation of application Ser. No. 07/773,969, filed Nov. 15, 1991, now abandoned which is based on International Application No. PCT/SE90/00324, filed on May 15, 1990.

FIELD OF THE INVENTION

The present invention relates to a disposable absorbent article, such as a disposable diaper or an incontinence guard, which comprises an inner liquid-permeable casing layer which when the article is worn, lies nearest the body of the wearer, an outer liquid-impermeable casing layer or backing sheet, and an absorbent pad which is enclosed between the two casing layers.

BACKGROUND OF THE INVENTION

By suitable selection of absorbent material, such as a combination of cellulose-fluff and so-called superabsorbent material, and by appropriate treatment of these materials, such as compression of the fluff material, it is possible to provide such absorbent articles with absorbent pads which possess a satisfactory total absorption capacity, by which is meant the maximum amount of liquid that can be absorbed throughout the whole of the pad. Any leakage experienced when using such products is therefore normally due to the fact that an excessive amount of liquid has been excreted locally onto the pad too rapidly for the capillaries in the fluff material to be able to transport the liquid to drier parts of the absorption pad quickly enough and/or because the superabsorbents are not able to "swell" sufficiently rapidly to absorb locally all of the liquid excreted. In other words, the liquid dispersion rate in the product is too low to be able to carry away large quantities of liquid from the wetting location with sufficient speed, by wetting location being meant the location in which the liquid is excreted onto the article. Under these conditions, the liquid will spread on the outer surface of the inner casing material and if the inner casing material should be inadvertently creased or folded when putting on the article, these creases or folds will be liable to function as a liquid flow channels and therewith result in leakage. It will be understood that the risk of leakage is greatest in the crotch area of the article, partly because the wetting location lies in this region of the article and partly because the absorbent pad is normally narrowest at this location. Furthermore, the crotch part of the absorbent pad normally always becomes deformed when the article is worn.

It is know from publication GB 2 124 907 that in the case of an article of the aforedescribed kind, the rate at which liquid is dispersed within an absorbent pad can be increased by incorporating in the pad a body of foamed-plastic material of very high liquid-permeability. The foamed-plastic body has a part which extends to the surface of the absorbent pad and which lies within the region of the wetting location when the article is worn. When liquid is excreted, the liquid flows through the part of the foam-plastic body located at the wetting location and when the absorbent pad is saturated locally, the liquid disperses quickly to dry parts of the pad through the agency of the foamed-plastic material. Publication EP 122 803 describes a similar article. Thus, the inclusion of such foamed-plastic bodies in articles of this kind will greatly increase the rate at which liquid is dispersed in the absorbent pad, although leakage can still nevertheless occur, for instance when the article concerned is an adult incontinence guard where the amount of liquid excreted, almost instantaneously, may be very large. The object of the present invention is to provide an absorbent disposable article whose absorbent pad has a high liquid dispersion rate and which is capable of absorbing large quantities of instantaneously excreted fluid.

SUMMARY OF THE INVENTION

This object is achieved in accordance with the invention with an absorbent disposable article of the aforedescribed kind which is characterized in that the absorbent pad includes in at least the region which forms the crotch part of the article when said article is worn a hose-like body of shape-stable material and of high liquid permeability, and in that the hose-like body is placed centrally in the pad and extends in the longitudinal direction of the article and border on the inner casing layer and is surrounded by absorbent material at least on the side thereof remote from said inner casing layer.

The hose-like body enables the liquid excreted to be carried away from the wetting location very quickly, therewith enabling large parts of the absorbent pad material to be utilized rapidly. Furthermore, when a large quantity of liquid is excreted at one and the same time, the interior space of the hose-like body will function as a liquid storage space, therewith enhancing the ability of the article to take-up large quantities of liquid at any one time. Because the hose-like body is made from a shape-stable, liquid-permeable material, the hose-like body will constantly maintain a tubular shape, not withstanding the deformation to which the article is always subjected in the crotch part of the article when said article is placed in position on the wearer and during the subsequent use of said article, and consequently the internal space of the hose-like body can be utilized to take-up liquid and to ensure that excreted liquid will always be distributed in a suitable fashion. All of these factors combine to provide an absorbent, disposable article which, in accordance with the invention, is able to absorb large quantities of liquid with a high degree of reliability against leakage.

BRIEF DESCRIPTION OF THE DRAWING FIGURES

These and other features of the invention and advantages afforded thereby will be evident from the following detailed description of a preferred exemplifying embodiment of an inventive disposable absorbent article, said description being made with reference to the accompanying drawings, in which.

DETAILED DESCRIPTION OF THE PREFERRED EMBODIMENT

Figure 1:
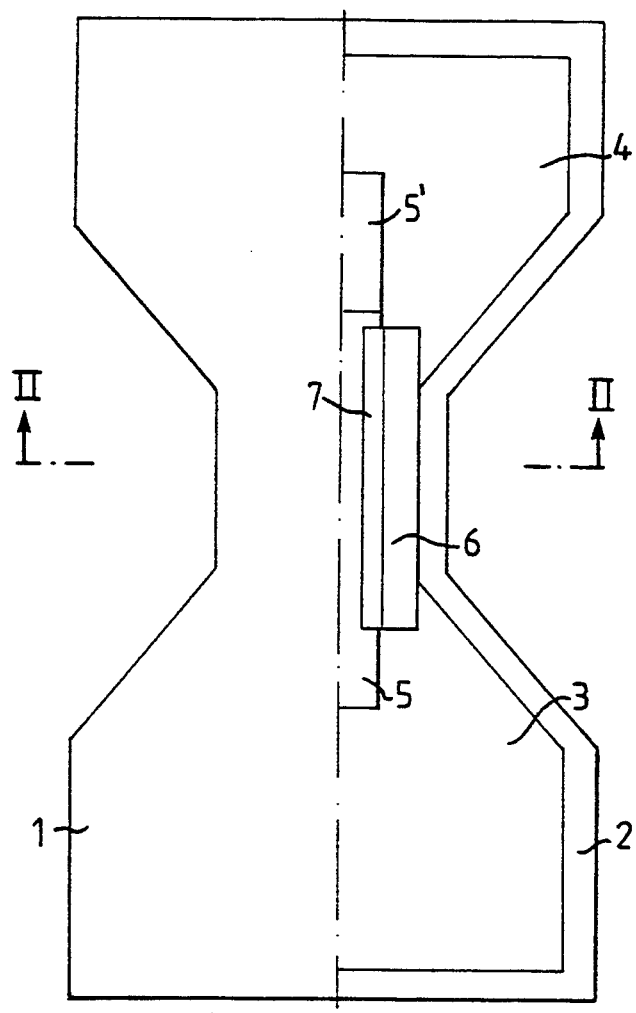
FIG. 1 is a view from above of an inventive diaper in which the inner casing layer has been partially removed.
Figure 2:
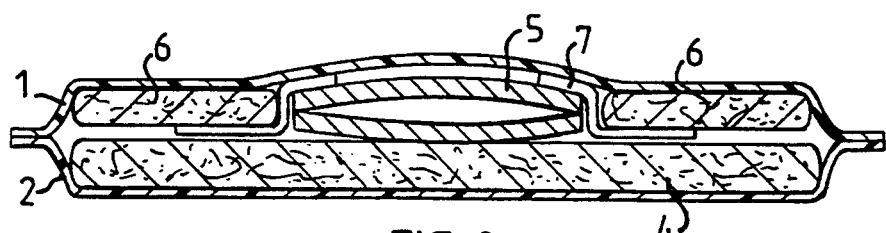
FIG. 2 is a sectional view taken on the line II—II in FIG. 1.
Figure 3:
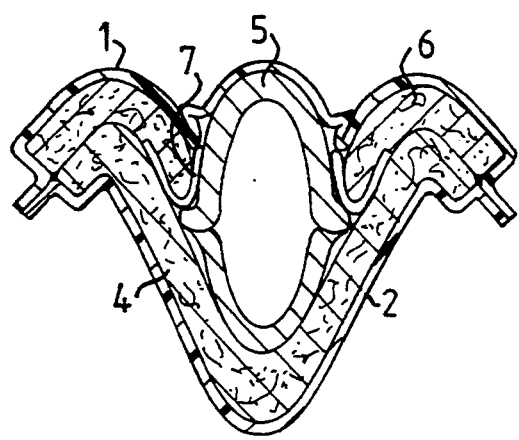
FIG. 3 is a sectional view similar to that of FIG. 2 but with the diaper placed in position on the wearer.

The diaper illustrated in FIGS. 1-3 includes, in a conventional manner, an inner liquid-permeable casing layer or sheet 1, which lies nearest the body of the wearer when the diaper is worn, and an outer liquid-impermeable casing layer or backing sheet 2. The inner and outer casing sheets are normally made of a non-woven fibre material and polyethylene or polypropylene plastic material respectively. The inner and outer casing sheets enclose therebetween an absorbent pad 3 and are mutually joined together along those regions located externally of the absorbent pad.

The pad 3 is comprised of two mutually different layers. The outer layer comprises a highly-absorbent, hour-glass body 4. The inner layer comprises a central, hose-like body 5 made of a shape-stable material of very high liquid-permeability and two side-bodies 6 of rapidly-absorbing material. Examples of material from which the highly-absorbent body 4 can be made include so-called superabsorbents, compressed cellulose-fluff material or combinations of superabsorbents and cellulose-fluff materials or tissue. By rapidly-absorbing material is meant material which can absorb a limited quantity of liquid very rapidly. The rapidly-absorbing material may, for instance, comprise cellulose-fluff material which has large capillaries and which has not been compressed or compressed to only a slight degree. Such material, however, is not able to absorb the same amount of liquid per unit volume as the aforesaid material in the highly-absorbent body 4.

The shape-stable, liquid-permeable material in the hose-like body 5 preferably comprises fibre wadding in which the fibres are bound together in some suitable manner, for instance by thermo bonding, with the aid of a binding agent or are bound mechanically, so as to obtain a three-dimensional fibre structure. The fibre wadding may be comprised of natural fibres and other biodegradable fibres or of polyester, polypropylene or polyethylene fibres or mixtures of these fibres.

Although it is preferred to construct the hose-like body 5 from fibre wadding, it will be understood that foamed plastic, such as polyether foam, polyester foam or polyurethane foam can be used, as disclosed in the earlier mentioned publications GB 2 134 907 and in EP 122 803.

FIG. 3 illustrates schematically how the diaper is deformed in the crotch part thereof subsequent to being placed on the wearer. As illustrated in this Figure, the hose-like body 5 will remain tubular, which means that the free space located inwardly of the walls of the hose-like body will increase. This is an important consequence of the configuration of said body, since this space functions as a storage space for excreted liquid, as explained in more detail hereinafter. Furthermore, the upper part of the hose-like body obtains an outwardly convex shape, which means that the uppermost part of the upper part of the body will lie against the body of the wearer within the region of the wetting location, particularly when the wearer is a female. This will ensure that excreted liquid will be distributed advantageously within the absorbent pad, with the aid of the hose-like body.

If a large quantity of liquid is excreted instantaneously onto the wetting location, the liquid will flow through the outwardly convex upper part of the hose-like body, into the internal free space of said body, through the lower outwardly concave part of said body and into the highly-absorbent body 4 of hour-glass configuration. Because the absorption rate in the body 4 is not sufficiently high for large quantities of liquid to be absorbed rapidly, not all of the liquid excreted can flow into the body 4 and liquid will therefore fill the lowermost part of the hose-like body and also a part of the internal space thereof. The liquid-dispersing properties of the material in the hose-like body therewith cause liquid to be dispersed in the longitudinal direction of said body in the lowermost part thereof, therewith enabling liquid to be dispersed to drier parts of the body 4 of hour-glass configuration, and enable a larger part of the total absorption capacity of said body to be utilized. That part of the liquid excreted at one and the same time which is not immediately dispersed in the aforesaid manner will initially be stored in the interior space of the hose-like body and subsequently absorbed by the body 4 of hour-glass configuration at the same rate as the slower absorption rate of said body.

For the purpose of additionally guiding the flow of excreted liquid, two liquid barriers 7 are provided on respective sides of the hose-like body 5 between said body and the side-bodies 6. In the illustrated embodiment, these barriers simply comprise strips of liquid-impervious plastic, although the barriers may, of course, have other configurations within the scope of the inventive concept. For instance, the barriers may be provided by appropriate treatment of corresponding surfaces of the side-bodies 6. Neither need the barriers be totally liquid-impervious. The only essential criterion in this respect is that the liquid-permeability of the barriers is considerably less than the permeability of the hose-like body.

The function of the barriers 7 is to prevent liquid from flowing laterally from the hose-like body and into the side-bodies 6, so as to ensure that the excreted liquid will be absorbed primarily by the body 4 of hour-glass configuration. This reduces the risk of lateral leakage when the interior space of the hose-like body is filled to a high level. It is mentioned in this regard that the slope of the surface of the liquid held in the internal space of the hose-like body will, of course, depend on the attitude of the wearer's body, and hence the barriers also have a sealing function to reduce the risk of lateral leakage due to the slope of the liquid surface or to splashing of the liquid as a result of movement of the wearer. If these barriers are not provided, it is possible that the rapidly-absorbing side-bodies 6 will become saturated when coming into contact with the relatively large quantity of liquid stored within the hose-like body, resulting in lateral leakage. Furthermore, the side-bodies are provided with the intention of taking-up any liquid which may run on the surface of the inner casing sheet 1, so as to further reduce the risk of lateral leakage. This safety function would thus be jeopardized if the barriers 7 were not provided. It should be mentioned, however, that because of the presence of the inventive hose-like body 5 the risk of liquid escaping onto the inner casing sheet is very small, and consequently the provision of side bodies 6 and barriers 7 constitutes a preferred, but not absolutely necessary safety facility.

Figure 4:
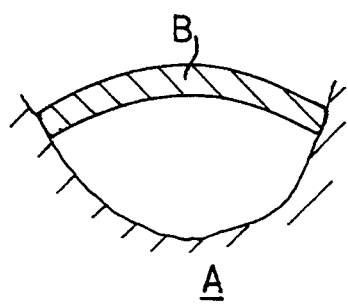
FIGS. 4 and 5 illustrate examples of the manner in which a sheet-like body of shape-stable material can be deformed when putting-on a diaper.
Figure 5:
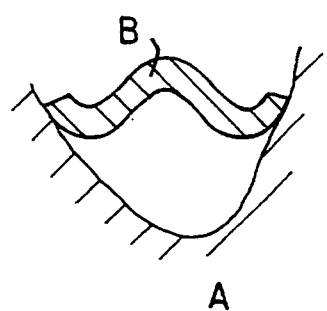

FIGS. 4 and 5 illustrate two examples of how a sheet-like body B comprising a form-stable, liquid-permeable material can be deformed when placing a diaper A on a wearer and while the diaper is being worn. The dispersion properties of the body B cannot be utilized in both of these cases, which greatly increases the risk of leakage. By forming the body 5 of highly liquid-permeable material to a hose-like configuration, it is ensured that the body will obtain a tubular configuration in the deformed state of a worn diaper irrespective of whether the compression forces to which the diaper is subjected when worn are symmetrical or not, which means that its lowermost part will always be in contact with liquid stored in the internal space of the hose-like body and that the liquid-dispersing properties of said body can thereby be utilized. Furthermore, because the uppermost part of the hose-like body has an outwardly convex shape, said uppermost part will abut the body of the wearer in the region of the wetting location, which ensures that the liquid excreted will be dispersed in the manner intended. Another contributory factor, in this regard, is that the aforesaid materials from which the hose-like body 5 can be made are all shape-stable in both a dry and wet state and have elastically restoring properties, i.e. when compressed they strive to return to their original form subsequent to the removal of the compressing force. When the diaper is worn by a member of the female sex, the uppermost part of the hose-like body will thus press against the genitals of the wearer, which ensures that the liquid excreted will always be deposited immediately into the hose-like body.

The hose-like body of the illustrated embodiment is manufactured by bonding two, flat elongated sheet-like bodies of bound fibre wadding along the edge margins thereof in some suitable manner, e.g. as by welding or gluing. Naturally, other methods of producing a hose-like body are conceivable, such as folding together an elongated, sheet-like material and securing the material along the two free edges thereof. The hose-like body is deformed to its tubular shape solely in the crotch part of the diaper, and the internal space of said body will therefore decrease successively and finally terminate completely in parts of the hose-like body located outwardly of the crotch-part. Consequently, the body 5 made of shape-stable, liquid-permeable material need not have the form of a hose throughout the whole of its length and a sheet-like part of the body 5 is indicated at 5' in FIG. 1. In accordance with one variant, the body 5 may, of course, initially have the tubular form illustrated in FIG. 3 and the expression "hose-like" used in the claims is not restricted to the hose-shape illustrated in FIG. 2.

In summary, the invention provides a disposable absorbent article which is able to take-up a large quantity of instantaneously excreted liquid, with a good margin of safety against leakage. The hose-like body 5 will always be deformed in the manner desired when the article is placed on a wearer and will therefore positively achieve good dispersion and distribution of the excreted liquid throughout the absorbent material of the absorbent pad, while at the same time the internal space of the hose-like body will form a storage space for that excreted liquid which is not absorbed immediately by the hose-like body or by the absorbent pad material. Because the hose-like body is positioned centrally, the body will always lie within the region of the wetting location and the elastic restoring properties of the material from which the hose-like body is made will ensure that the inventive article will conform very-readily to the body contours of the wearer, which together with the very high liquid-permeability of the hose-like body will ensure that excreted liquid is transported into the absorbent parts of the article in a desirable manner. The elastic restoring properties of the hose-like body also ensure that the side-parts of the article will be pressed sealingly against the thighs of the wearer when the article is worn.

It will be understood that such an article is particularly suitable for use as an incontinence guard for adult women. However, the invention can also be applied to advantage in conjunction with diapers for both large and small children. When the invention is applied in children's diapers, the ability to absorb large quantities of liquid excreted at one and the same time is not of a primary interest, and the liquid-dispersion and leakage-safety properties of the diaper are decisive for such an application.

It will be understood that the illustrated embodiment can be modified in many ways within the scope of the normal expertise of one skilled in this art. For instance, the hose-like body can be enveloped by an homogenous layer of absorbent material, instead of being surrounded by separate absorbent pads as in the illustrated embodiment. Furthermore, the shapes and dimensions of the parts incorporated in the absorbent pad can be varied. In particular, the upper layer of the absorbent pad may comprise a body of absorbent material having a shape which coincides with the body forming the bottom layer and provided with a central recess in which the hose-like body is placed, and the side-bodies and liquid barriers can be excluded, as before mentioned. Furthermore, the casing material and the parts incorporated in the absorbent body can be joined together in different ways without departing from the concept of the invention. The scope of the invention is therefore only limited by the content of the following claims.

We claim:

1. A disposable absorbent article that includes a crotch part which lies in the region of the crotch of the body of the wearer when the article is worn, said article comprising an inner liquid-permeable casing sheet which lies nearest the body of the wearer when the article is worn, an outer liquid-impermeable casing sheet and an absorbent pad enclosed between said inner and outer casing sheets, the absorbent pad, at least within the crotch part of the absorbent article, including a tubular body comprised of a shape-stable material of very high liquid-permeability, the tubular body being centrally positioned and extending in the longitudinal direction of the article and being surrounded by absorbent material on at least the side thereof remote from the inner sheet, a part of the tubular body facing the wearer during use of the article having an outwardly convex shape abutting the body of the wearer in the region of a wetting location when the article is worn.

2. A disposable absorbent article according to claim 1, wherein the shape-stable material of the tubular body has elastically restoring properties such that, when compressed, it strives to return to its original form subsequent to removal of a compressing force.

3. A disposable absorbent article according to claim 1, wherein the tubular body is made of a material which is shape-stable both in a dry and a wet state.

4. An article according to claim 1, wherein the tubular body is made of fibre wadding in which the fibres are bound together to form a three-dimensional fibre structure.

5. An article according to claim 1, wherein the tubular body is made of a foamed-plastic material.

6. An article according to claim 5, wherein the foamed-plastic material is a polyether plastic.

7. An article according to claim 5, wherein the foamed-plastic material is a polyester plastic.

8. An article according to claim 5, wherein the foamed-plastic material is a polyethane plastic.

9. An article according to claim 1 wherein the absorbent material on at least the side of the tubular body remote from the inner casing sheet comprises a body of highly-absorbent material having an hour-glass configuration which lies nearest the outer casing sheet, and two side-bodies of rapidly-absorbing material located on opposite lateral sides of the tubular body.

10. An article according to claim 1, including two liquid barriers bordering on respective opposite lateral sides of the tubular body.

11. An article according to claim 10, wherein the liquid barriers are comprised of strips of liquid-impervious plastic material.

12. An article according to claim 9, including two liquid barriers bordering on respective opposite lateral sides of the tubular body, and each liquid barrier separating one of the side-bodies from the tubular body.

13. An article according to claim 12, wherein the liquid barriers are comprised of strips of liquid-impervious plastic material.

* * * * *